(12) United States Patent
Umemoto et al.

(10) Patent No.: US 7,265,247 B1
(45) Date of Patent: Sep. 4, 2007

(54) SUBSTITUTED PHENYLSULFUR TRIFLUORIDE AND OTHER LIKE FLUORINATING AGENTS

(75) Inventors: Teruo Umemoto, Westminster, CO (US); Yong Xu, Salt Lake City, UT (US)

(73) Assignee: IM&T Research, Inc., Denver, CO (US)

( * ) Notice: Subject to any disclaimer, the term of this patent is extended or adjusted under 35 U.S.C. 154(b) by 0 days.

(21) Appl. No.: 11/494,983

(22) Filed: Jul. 28, 2006

(51) Int. Cl.
*C07C 321/00* (2006.01)
(52) U.S. Cl. .......................................... 568/23; 568/18
(58) Field of Classification Search ............... 568/23, 568/18
See application file for complete search history.

(56) References Cited

U.S. PATENT DOCUMENTS 7,087,681 B2    8/2006   Umemoto

FOREIGN PATENT DOCUMENTS

GB      2 276 379    *  9/1994

JP      P2000-38370 A    7/2000

OTHER PUBLICATIONS

Shephpard, {Alkyl- and Arylsulfur Trifluorides, Journal of the American Chemical Society (1962), 84, 3058-3063}.*
Calamari (1979) C&EN Letters March 19 p. 4.
Kobayashi (2004) Tetrahedron 60 p. 6923.
Lal (1999) Chem. Commun. p. 215.
Middleton (1974) J. Org. Chem. 40 p. 574.
Olah (1973) J. Ameri. Chem. Soc. 96 p. 925.
Organic Reactions- Methods to Prepare Monofluoroalphatic Compounds p. 158.
Pashinnik (2003) Synthetic Communications 33 p. 2505.
Sheppard (1962) J. Chem. Soc. 84 p. 3058.
Sheppard (1972) J. Fluorine Chem. 2 p. 53.
Tullock (1960) Monaish. Chem. 88 p. 539.
Unknown (1981) Acta Chimica Sinica 39 p. 64.

* cited by examiner

*Primary Examiner*—Thurman Page
*Assistant Examiner*—Chukwuma Nwaonicha
(74) *Attorney, Agent, or Firm*—Swanson & Bratschun, L.L.C.

(57) ABSTRACT

Novel substituted phenylsulfur trifluorides that act as fluorinating agents are disclosed. Also disclosed are methods for their preparation and methods for their use in introducing one or more fluorine atoms into target substrate compounds.

16 Claims, No Drawings

SUBSTITUTED PHENYLSULFUR TRIFLUORIDE AND OTHER LIKE FLUORINATING AGENTS

TECHNICAL FIELD

The present invention relates to fluorinating agents and more particularly to novel substituted phenylsulfur trifluorides that act as fluorinating agents.

BACKGROUND OF THE INVENTION

Fluorine-containing compounds have found wide use in medical, agricultural and other like industries (see Chemical & Engineering News, June 5, pp 15-32 (2006)). These compounds show specific biologic activity based on the presence of one or more fluorine atoms. A particular drawback in their usefulness is the scarcity of natural fluorine-containing compounds, requiring most such compounds to be prepared through organic synthesis.

Fluorinating agents are compounds that selectively introduce fluorine atom(s) into target compounds through one or more chemical reactions to produce fluorine-containing compounds. Particularly useful fluorinating agents have the capacity to replace oxygen or oxygen-containing groups in the target compound with fluorine. A number of fluorinating agents have been discovered; however, as discussed in more detail below, all of these agents have significant drawbacks based on safety, reactivity, storage stability, and/or disposability.

Illustrative examples of known fluorinating agents include: sulfur tetrafluoride ($SF_4$), a highly toxic gas that is often utilized under pressure (J. Am. Chem. Soc., Vol. 82, pp 543-551 (1960)); N,N-diethylaminosulfur trifluoride (DAST), an unstable liquid agent having a highly explosive nature, i.e., low thermal stability and large amounts of thermal energy upon decomposition (J. Org. Chem., Vol. 40, pp 574-578 (1975) and Chem. & Eng. News, Vol. 57, No. 19, p 4 (1979)); bis(methoxyethyl)aminosulfur trifluoride (Deoxo-Fluor®) a product having greater thermal stability than DAST but still having a starting decomposition temperature similar to DAST (Chemical Communications, pp 215-216 (1999)); selenium tetrafluoride ($SeF_4$), a highly toxic selenium compound (J. Am. Chem. Soc., Vol. 96, pp 925-927 (1974)); and various other more designed fluorinating agents that provide greater safety but have provided substantially reduced reactivity and yields: phenylfluorophosphane reagents ($Ph_nPF_{5-n}$ (n=1~3), Chem. Pharm. Bull., Vol. 16, p 1009 (1968), α,α-difluoroalkyamino reagents (ClCFHCF$_2$NEt$_2$, Organic Reactions, Vol. 21, pp 158-173 (1974)), 2,2-difluoro-1,3-dimethylimidazolindine (Jpn. Kokai Tokkyo Koho JP 2000 38,370), and [(m-methylphenyl)difluoromethyl]diethylamine (Tetrahedron, Vol. 60, pp 6923-6930).

In addition, phenylsulfur trifluoride has also been synthesized and used as a fluorinating agent, but its fluorination yields have proven low (J. Am. Chem. Soc., Vol. 84, pp 3058-3063 (1962)). Pentafluorophenylsulfur trifluoride was also synthesized and used as a fluorinating agent, but has proven costly, since its starting material is expensive and it has only two reactive fluorine atoms out of eight existing in the molecule (J. Fluorine Chem., Vol. 2, pp 53-62 (1972/73)). More recently, p-nitrophenylsulfur trifluoride was examined and also shown to have little or no fluorination ability (Acta Chimica Sinica, Vol. 39, No. 1, pp 63-68 (1981)).

Each of these conventional illustrative fluorinating agents requires room for improvement on providing more effective and safer reagents for use in the production of these important fluorine-containing compounds.

As such, there is a need in the field to provide safe, reactive, less hazardous, cost effective, fluorinating agents, especially fluorinating agents that selectively introduce fluorine atoms into compounds by replacement of oxygen or oxygen-containing groups with fluorine atoms. Ideally, these fluorinating agents provide high yields and can be handled and stored in a safe manner.

The present invention is directed toward overcoming one or more of the problems discussed above.

SUMMARY OF THE INVENTION

The present invention provides novel fluorinating agents for use in the introduction of fluorine atoms into target compounds. The resultant target compounds, i.e., fluorine-containing compounds, have been shown to have tremendous potential in medical, agricultural, and other like uses.

In general, fluorinating agents of the invention are novel substituted phenylsulfur trifluoride compounds. The substituted phenylsulfur trifluoride compounds are shown herein to have substantial functional and safety benefits over conventional fluorinating agents.

The present invention also provides synthesis schemes for the novel compounds of the invention, and data illustrating the use of these agents in preparing various fluorine-containing compounds.

DETAILED DESCRIPTION OF THE INVENTION

The present invention provides novel fluorinating agents for use in introducing fluorine atoms into target compounds. For use in the present invention the term "target compound" includes any substrate that once fluorinated is useful in the medical, agricultural, biological or other like field, i.e., is a fluorine-containing compound. In preferred instances, the target compound(s) of the invention include one or more oxygen atom(s) and/or one or more oxygen-containing group(s) for selective replacement by the fluorine atom(s). Illustrative target compounds include alcohols, aldehydes, ketones, carboxylic acids, acid halides, esters, acid anhydrides, amides, imides, epoxides, lactones, lactams, sulfides, sulfoxides, sulfonic acids, phosphines, phosphine oxides, and phosphonic acids.

Embodiments of the invention are novel substituted phenylsulfur trifluorides. Novel substituted phenylsulfur trifluorides are shown herein to be potent agents for selectively introducing fluorine atoms into target compounds thereby producing fluorine-containing compounds.

Fluorinating agents of the present invention show high thermal stability, having high decomposition temperatures and low exothermic heat (−ΔH) values as compared to conventional agents (see Examples below). In addition, fluorinating agents of the invention are highly reactive with a number of different target compounds, typically providing high yields of fluorine-containing product compounds. The high stability and reactivity of the present invention's compounds is unexpected when compared to those of conventional fluorinating agents, i.e., DAST, Deoxo-Fluor® etc.

Embodiments of the invention also provide methods for preparing the fluorinating agents and for using the fluorinating agents in the preparation of fluorine-containing compounds.

The invention provides compounds of the formula (I):

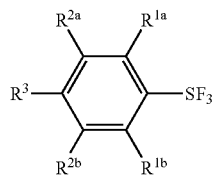

in which $R^{1a}$ and $R^{1b}$ can independently be a hydrogen atom or a primary or secondary alkyl group having from one to eight carbon atoms;

$R^{2a}$ and $R^{2b}$ can independently be a hydrogen atom or a primary, secondary, or tertiary alkyl group having from one to eight carbon atoms;

and $R^3$ is a hydrogen atom, a halogen atom, or a primary, secondary, or tertiary alkyl group having from one to eight carbon atoms, provided that, when $R^3$ is a hydrogen atom, at least two of $R^{1a}$, $R^{1b}$, $R^{2a}$, and $R^{2b}$ are primary, secondary, or tertiary alkyl groups having from one to eight carbon atoms and the others are a hydrogen atom, and when $R^3$ is a primary alkyl group having from one to eight carbon atoms, at least one of $R^{1a}$, $R^{1b}$, $R^{2a}$, and $R^{2b}$ is a primary, secondary, or tertiary alkyl group having from one to eight carbon atoms and the other R groups are a hydrogen atom, and when at least two of $R^{2a}$, $R^{2b}$ and $R^3$ are tertiary alkyl group, the tertiary alkyl groups are non-adjacent. In preferred embodiments of formula (I), the alkyl groups have from one to four carbon atoms.

Some embodiments of the invention are those compounds of formula (I) where primary or secondary alkyl groups of $R^{1a}$ and $R^{1b}$ having from one to eight carbon atoms include: $CH_3$, $CH_2CH_3$, $CH_2(CH_2)_nCH_3$ (n=1-6), $CH(CH_3)_2$, $CH(CH_3)CH_2CH_3$, $CH(CH_3)CH_2(CH_2)_nCH_3$ (n=1-4), $CH_2CH(CH_3)_2$, and $CH_2C(CH_3)_3$. More preferred primary or secondary alkyl groups of $R^{1a}$ and $R^{1b}$ include: $CH_3$, $CH_2CH_3$, $CH_2(CH_2)_nCH_3$ (n=1 or 2), $CH(CH_3)_2$, and $CH_2CH(CH_3)CH_3$, and most preferred primary or secondary alkyl groups are $CH_3$ and $CH(CH_3)_2$.

Other embodiments of the invention are those fluorinating agents where primary, secondary, or tertiary alkyl groups having from one to eight carbon atoms of $R^{2a}$ and/or $R^{2b}$ include: $CH_3$, $CH_2CH_3$, $CH_2(CH_2)_nCH_3$ (n=1-6), $CH(CH_3)_2$, $CH(CH_3)CH_2CH_3$, $CH(CH_3)CH_2(CH_2)_nCH_3$ (n=1-4), $C(CH_3)_3$, $C(CH_3)_2CH_2CH_3$, $C(CH_3)_2CH_2(CH_2)_nCH_3$ (n=1-3), $CH_2CH(CH_3)_2$, and $CH_2C(CH_3)_3$. More preferred alkyl groups having from one to eight carbon atoms of $R^{2a}$ and/or $R^{2b}$ include: $CH_3$, $CH_2CH_3$, $CH_2(CH_2)_nCH_3$ (n=1 or 2), $CH(CH_3)_2$, $CH_2CH(CH_3)CH_3$ and $C(CH_3)_3$, and most preferred primary, secondary, or tertiary alkyl groups are $CH_3$, $CH(CH_3)_2$, and $C(CH_3)_3$.

Other embodiments of the invention are those fluorinating agents where primary, secondary, or tertiary alkyl groups of $R^3$ having from one to eight carbon atoms include: $CH_3$, $CH_2CH_3$, $CH_2(CH_2)_nCH_3$ (n=1-6), $CH(CH_3)_2$, $CH(CH_3)CH_2CH_3$, $CH(CH_3)CH_2(CH_2)_nCH_3$ (n=1-4), $C(CH_3)_3$, $C(CH_3)_2CH_2CH_3$, $C(CH_3)_2CH_2(CH_2)_nCH_3$ (n=1-3), $CH_2CH(CH_3)_2$, and $CH_2C(CH_3)_3$. More preferred primary, secondary, or tertiary alkyl groups of $R^3$ having from one to eight carbon atoms include: $CH_3$, $CH_2CH_3$, $CH_2(CH_2)_nCH_3$ (n=1 or 2), $CH(CH_3)_2$, $CH_2CH(CH_3)CH_3$ and $C(CH_3)_3$, and most preferred primary, secondary, or tertiary groups are $CH_3$, $CH(CH_3)_2$, and $C(CH_3)_3$.

When used herein, the term "halogen atom" or "halo" include fluorine, chlorine, bromine and iodine and fluoro, chloro, bromo, and iodo, respectively.

Examples of preferred halogen atoms of R include: fluorine, chlorine, bromine or iodine atoms, among these halogen types, fluorine, chlorine or bromine are more preferred, and fluorine and chlorine are most preferred.

When used herein, the term "alkyl" includes all straight and branched isomers. Representative examples of these types of groups include methyl, ethyl, propyl, isopropyl, butyl, isobutyl, tert-butyl, sec-butyl, penty, hexyl, heptyl, and octyl.

Table 1 provides illustrative combinations of $R^{1a}$, $R^{1b}$, $R^{2a}$ and $R^3$ for inclusion in formula (I).

TABLE 1

Illustrative Examples of Substituted Phenylsulfur Trifluoride Compounds of Formula (I) Showing $R^{1a}$, $R^{1b}$, $R^{2a}$, $R^{2b}$, and $R^3$ Combinations Based On Substitutions Into Formula (I)

| $R^{1a}$ | $R^{1b}$ | $R^{2a}$ | $R^{2b}$ | $R^3$ |
|---|---|---|---|---|
| H | H | H | H | $C(CH_3)_3$ |
| H | H | H | H | $C(CH_3)_2C_2H_5$ |
| H | H | H | H | $C(CH_3)_2(CH_2)_2CH_3$ |
| H | H | H | H | $C(CH_3)_2(CH_2)_3CH_3$ |
| H | H | H | H | $C(CH_3)_2(CH_2)_4CH_3$ |
| H | H | $C(CH_3)_3$ | $C(CH_3)_3$ | H |
| $CH_3$ | H | H | H | $C(CH_3)_3$ |
| $CH_3$ | $CH_3$ | H | H | $C(CH_3)_3$ |
| $C_2H_5$ | $C_2H_5$ | H | H | $C(CH_3)_3$ |
| $CH_2CH_2CH_3$ | $CH_2CH_2CH_3$ | H | H | $C(CH_3)_3$ |
| $CH_2(CH_2)_2CH_3$ | $CH_2(CH_2)_2CH_3$ | H | H | $C(CH_3)_3$ |
| $CH_3$ | $CH_3$ | $CH_3$ | H | $C(CH_3)_3$ |
| $CH_3$ | $CH_3$ | $CH_3$ | $CH_3$ | $C(CH_3)_3$ |
| H | H | H | H | $CH(CH_3)_2$ |
| H | H | H | H | $CH(CH_3)C_2H_5$ |
| $CH_3$ | H | H | H | $CH(CH_3)_2$ |
| $CH_3$ | $CH_3$ | H | H | $CH(CH_3)_2$ |
| $CH(CH_3)_2$ | $CH(CH_3)_2$ | H | H | $CH(CH_3)_2$ |
| $CH(CH_3)_2$ | $CH(CH_3)_2$ | H | H | $C(CH_3)_3$ |
| $CH_3$ | $CH_3$ | H | H | H |
| $CH_3$ | H | H | $CH_3$ | H |

TABLE 1-continued

Illustrative Examples of Substituted Phenylsulfur Trifluoride Compounds of Formula (I) Showing $R^{1a}$, $R^{1b}$, $R^{2a}$, $R^{2b}$, and $R^3$ Combinations Based On Substitutions Into Formula (I)

| $R^{1a}$ | $R^{1b}$ | $R^{2a}$ | $R^{2b}$ | $R^3$ |
|---|---|---|---|---|
| $CH_3$ | H | H | H | $CH_3$ |
| H | H | $CH_3$ | $CH_3$ | H |
| $CH_3$ | $CH_3$ | H | H | $CH_3$ |
| $CH_3$ | $CH_3$ | $CH_3$ | H | $CH_3$ |
| $CH_3$ | $CH_3$ | $CH_3$ | $CH_3$ | $CH_3$ |
| $C_2H_5$ | $C_2H_5$ | H | H | H |
| $C_2H_5$ | $C_2H_5$ | H | H | $C_2H_5$ |
| $C_2H_5$ | $C_2H_5$ | H | H | $C(CH_3)_3$ |
| $CH_2CH_2CH_3$ | $CH_2CH_2CH_3$ | H | H | $CH_2CH_2CH_3$ |
| $CH_2(CH_2)_2CH_3$ | $CH_2(CH_2)_2CH_3$ | H | H | $CH_2(CH_2)_2CH_3$ |
| $CH_2(CH_2)_3CH_3$ | $CH_2(CH_2)_3CH_3$ | H | H | $CH_2(CH_2)_3CH_3$ |
| $CH_2(CH_2)_4CH_3$ | $CH_2(CH_2)_4CH_3$ | H | H | $CH_2(CH_2)_4CH_3$ |
| $CH_2(CH_2)_5CH_3$ | $CH_2(CH_2)_5CH_3$ | H | H | $CH_2(CH_2)_5CH_3$ |
| $CH_2(CH_2)_6CH_3$ | $CH_2(CH_2)_6CH_3$ | H | H | $CH_2(CH_2)_6CH_3$ |
| H | H | H | H | F |
| H | H | H | H | Cl |
| H | H | H | H | Br |
| H | H | H | H | I |
| H | H | $CH_3$ | H | Cl |
| H | H | $CH_3$ | $CH_3$ | Cl |
| $CH_3$ | H | $CH_3$ | $CH_3$ | Cl |
| $CH_3$ | $CH_3$ | $CH_3$ | $CH_3$ | Cl |
| $CH_3$ | $CH_3$ | $CH_3$ | $CH_3$ | Br |
| $CH_3$ | $CH_3$ | $CH_3$ | $CH_3$ | F |

Preferred embodiments of formula (I) are compounds having a formula (II):

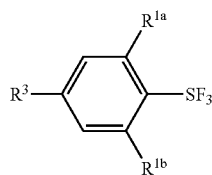

(II)

in which $R^{1a}$ and $R^{1b}$ are independently a hydrogen atom or a primary or secondary alkyl group having from one to eight carbon atoms; and $R^3$ is a hydrogen atom, a halogen atom, or a primary, secondary, or tertiary alkyl group having from one to eight atoms, provided that, when $R^3$ is a hydrogen atom, $R^{1a}$ and $R^{1b}$ are primary or secondary alkyl groups having from one to eight carbon atoms and, when $R^3$ is a primary alkyl group having from one to eight carbon atoms, at least one of $R^{1a}$ and $R^{1b}$ is a primary or secondary alkyl group having from one to eight carbon atoms and the other is a hydrogen atom. In preferred embodiments the alkyl groups of formula (II) have from one to four carbon atoms.

Table 2 provides illustrative combinations of $R^{1a}$, $R^{1b}$ and $R^3$ for inclusion in formula (II).

TABLE 2

Illustrative Examples of Substituted Phenylsulfur Trifluoride Compounds of Formula (II) Showing $R^{1a}$, $R^{1b}$, and $R^3$ Combinations Based On Substitutions Into Formula (II)

| $R^{1a}$ | $R^{1b}$ | $R^3$ |
|---|---|---|
| H | H | $C(CH_3)_3$ |
| H | H | $C(CH_3)_2C_2H_5$ |
| H | H | $C(CH_3)_2(CH_2)_2CH_3$ |
| H | H | $C(CH_3)_2(CH_2)_3CH_3$ |
| H | H | $C(CH_3)_2(CH_2)_4CH_3$ |
| $CH_3$ | H | $C(CH_3)_3$ |
| $CH_3$ | $CH_3$ | $C(CH_3)_3$ |
| H | H | $CH(CH_3)_2$ |
| H | H | $CH(CH_3)C_2H_5$ |
| $CH_3$ | H | $CH(CH_3)_2$ |
| $CH_3$ | $CH_3$ | $CH(CH_3)_2$ |
| $CH(CH_3)_2$ | $CH(CH_3)_2$ | $CH(CH_3)_2$ |
| $CH(CH_3)_2$ | $CH(CH_3)_2$ | $C(CH_3)_3$ |
| $CH_3$ | $CH_3$ | H |
| $CH_3$ | H | $CH_3$ |
| $CH_3$ | $CH_3$ | $CH_3$ |
| $C_2H_5$ | $C_2H_5$ | H |
| $C_2H_5$ | $C_2H_5$ | $C_2H_5$ |
| $C_2H_5$ | $C_2H_5$ | $C(CH_3)_3$ |
| $CH_2CH_2CH_3$ | $CH_2CH_2CH_3$ | $CH_2CH_2CH_3$ |
| $CH_2(CH_2)_2CH_3$ | $CH_2(CH_2)_2CH_3$ | $CH_2(CH_2)_2CH_3$ |
| $CH_2(CH_2)_3CH_3$ | $CH_2(CH_2)_3CH_3$ | $CH_2(CH_2)_3CH_3$ |
| $CH_2(CH_2)_4CH_3$ | $CH_2(CH_2)_4CH_3$ | $CH_2(CH_2)_4CH_3$ |
| $CH_2(CH_2)_5CH_3$ | $CH_2(CH_2)_5CH_3$ | $CH_2(CH_2)_5CH_3$ |
| $CH_2(CH_2)_6CH_3$ | $CH_2(CH_2)_6CH_3$ | $CH_2(CH_2)_6CH_3$ |
| H | H | F |
| H | H | Cl |
| H | H | Br |
| H | H | I |
| $CH_3$ | H | Cl |
| $CH_3$ | $CH_3$ | Cl |
| $CH_3$ | $CH_3$ | Br |
| $CH_3$ | $CH_3$ | F |

The fluorinating agents of the present invention are typically provided in substantially pure form, for example at least 50% pure, more typically 60% pure, advantageously at least 75% pure and preferably at least 85% pure. All percentages are calculated on a weight/weight basis.

It will be understood by one of skill in the relevant art that certain compounds of the invention may comprise one or more chiral centers so that the compounds may exist as stereoisomers, including diastereoisomers and enantiomers. It is envisioned that all such compounds be within the scope of the present invention, including all such stereoisomers, and mixtures thereof, including racemates.

Fluorinating agents of the invention may be prepared according to the methods as described in the Examples below, see particularly Example 2-15. In addition, methods reported in the literature may be modified to produce various agents illustrated in Tables 1 and 2 (see J. Am. Chem. Soc., Vol. 84, pp 3058-3063 (1962); Synthetic Communications, Vol. 33, No. 14, pp 2505-2509 (2003)).

Typically, the starting materials for synthesis of the substituted phenylsulfur trifluorides are the corresponding substituted biphenyl disulfides, which are either commercially available, prepared by oxidation of the corresponding substituted thiophenols, or are prepared from the corresponding substituted benzenesulfonyl halides (see for example the methods as shown Example 1).

While not being tied to any particular mechanism, the unexpected functional activities of the compounds of the present invention are due, at least in part, to their relatively high ability. The high stability of these compounds is due to high decomposition temperatures and low exothermal heat (−ΔH) (see Examples 16-25) as compared to more conventional fluorinating agents. These values can be compared to the values for other conventional fluorinating agents (see Table 4), where DAST and Deoxo-Fluor® have a decomposition temperature of about 140° C. and exothermic heat values of 1100-1700 J/g (as compared to compounds of the invention where decomposition temperatures of about 200-320° C. and exothermic heat of 350-700 J/g are typical (see Table 4).

EXAMPLES

The following examples are provided for illustrative purposes only and are not intended to limit the scope of the invention. Table 3 provides structure names and formulas for reference when reviewing the following examples:

TABLE 3

Preferred Substituted Phenylsulfur Trifluorides (Formulas IV-XIII) and Starting Materials (Formula III):

| Formula Number | Name | Structure |
|---|---|---|
| III | Bis(2,6-dimethyl-4-tert-butylphenyl) disulfide | 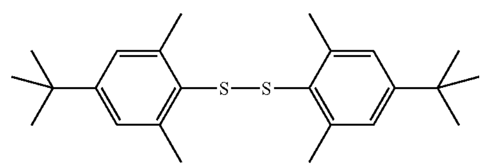 |
| IV | 2,6-dimethyl-4-tert-butylphenylsulfur trifluoride | 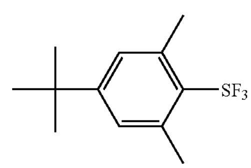 |
| V | 4-tert-butylphenylsulfur trifluoride | 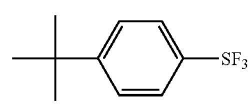 |
| VI | 2,4,6-trimethylphenylsulfur trifluoride | 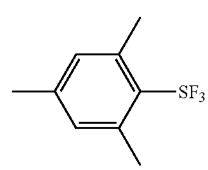 |
| VII | 2,4-dimethylphenylsulfur trifluoride | 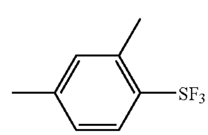 |

TABLE 3-continued

Preferred Substituted Phenylsulfur Trifluorides (Formulas IV-XIII) and Starting Materials (Formula III):

| Formula Number | Name | Structure |
|---|---|---|
| VIII | 2,5-dimethylphenylsulfur trifluoride | 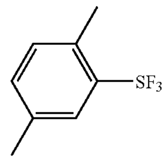 |
| IX | 2,6-dimethylphenylsulfur trifluoride | 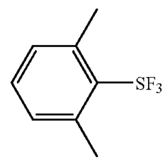 |
| X | 4-fluorophenylsulfur trifluoride | 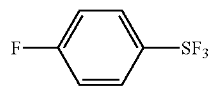 |
| XI | 4-chlorophenylsulfur trifluoride | 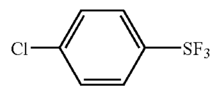 |
| XII | 3-methyl-4-chlorophenylsulfur trifluoride | 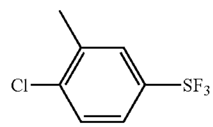 |
| XIII | 2,4,6-tri(isopropyl)phenylsulfur trifluoride | 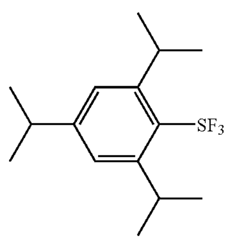 |

Example 1

Preparation of bis(2,6-dimethyl-4-tert-butylphenyl)disulfide

The following reaction scheme is provided as illustrative:

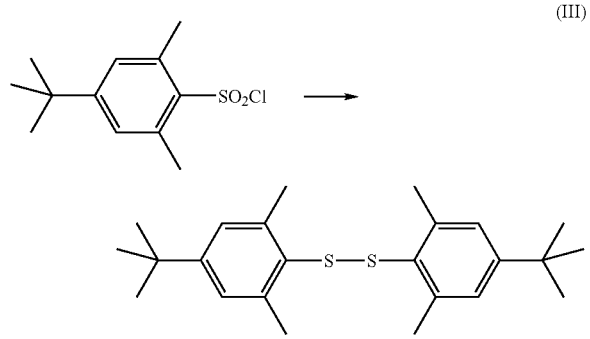

A two liter, three-neck flask, was obtained. A condenser with a drying tube, a thermometer, and a dropping funnel were each attached to the flask. Zinc dust (<10 micron, 43.6 g, 0.667 mol) and anhydrous tetrahydrofuran (400 ml) were added to the flask. The mixture was stirred and cooled on an ice-water bath and 58.6 ml (0.534 mmol) of titanium tetrachloride added drop wise (~45 minutes). During the entire addition of titanium tetrachloride, the temperature of the mixture was maintained below 25° C. Once the addition was complete, a solution of 2,6-dimethyl-4-tert-buylbenzenesulfonyl chloride (69.48 g, 0.267 mol) in 200 ml of anhydrous tetrahydrofuran was added drop wise (~60 minutes). During the entire addition of the material, the temperature of the mixture was maintained below 20° C. At the conclusion of the 2,6-dimethyl-4-tert-buylbenzenesulfonyl chloride addition, the ice-water bath was removed, the mixture was allowed to stir an additional 30 minutes. The mixture was then heated on an oil bath at 60° C. for four hours. The mixture was then cooled to room temperature and 800 ml of 1N hydrochloric acid and 300 ml of ice water added. The resultant pale yellow precipitates were collected by filtration and washed with water (300 ml×3). The precipitate was then dried under vacuum and the precipitates recrystallized from hexanes, giving 33.1 g bis(2,6-dimethyl-4-tert-butylphenyl) disulfide (see Formula III, Table 3). The yield of the reaction was 70% and the material had the following spectral data: $^1$H NMR (CDCl$_3$) δ 7.04 (s, 4H), 2.23 (s, 12H), 1.30 (s, 18H).

The present example illustrates the utility of the present invention for synthesizing fluorinating agents that can be used to produce fluorine-containing compounds.

Example 2

Synthesis Embodiment of 2,6-dimethyl-4-tert-butylphenylsulfur trifluoride, A Fluorinating Agent of the Present Invention The following reaction scheme is provided as illustrative for this example:

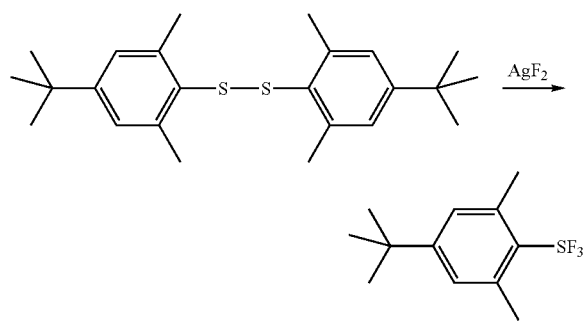

(IV)

A 100 ml fluoropolymer-round flask equipped with a magnetic stirrer, a thermometer and a solid addition funnel connected to a drying tube, was flushed with dry nitrogen and charged with 16.08 grams (g) (111 mmol) of silver difluoride and 20 ml of anhydrous 1,1,2-trichlorotrifluoroethane. Bis(2,6-dimethyl-4-tert-butylphenyl)disulfide (6.03 g, 16.3 mmol), charged in the solid addition funnel, was added to the stirred slurry in small portions to maintain the temperature of reaction mixture between 35 and 40° C. The addition of disulfide required approximately twenty minutes.

The reaction mixture was stirred for an additional thirty minutes at room temperature, and then heated to reflux for about five minutes. The reaction mixture was filtered under a blanket of dry nitrogen. After the evaporation of the solvent, the residue was distilled at reduced pressure to give the compound 2,6-dimethyl-4-tert-butylphenylsulfur trifluoride shown as Formula IV, Table 3 (bp 92-93° C./0.5 mmHg, mp 59.1° C. (by DSC)). The compound was a white solid, yield of 5.20 g (64%).

The spectral data of the material is as follows: $^{19}$F NMR (THF-d$_8$) δ 53.90 (d, J=60.7 Hz, 2F), −57.03 (t, J=60.7 Hz, 1F); $^1$H NMR (CD$_3$CN) δ 7.25 (s, 2H), 2.60 (s, 6H), 1.30 (s, 9H); $^{13}$C NMR (CD$_3$CN) δ 155.37 (s), 141.61 (s), 133.74 (s), 127.56 (s), 34.45 (s), 30.25 (s), 19.09 (s); MS (EI) m/z 149.0 (M$^+$+1-2F, 100.0), 250.1 (M$^+$, 1.8); HRMS (EI) for C$_9$H$_{11}$F$_3$S (M$^+$): found 250.101491, calcd 250.100307.

The present example illustrates the utility of the present invention for synthesizing fluorinating agents that can be used to produce fluorine-containing compounds.

Example 3

Synthesis Embodiment of 2,6-dimethyl-4-tert-butylphenylsulfur trifluoride, A Fluorinating Agent of the Present Invention The following reaction scheme is provided as illustrative for this example:

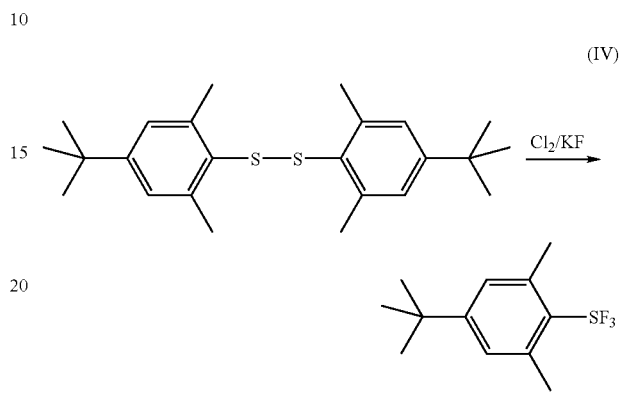

(IV)

Chlorine (Cl$_2$) was passed at 23 ml/min through a stirred mixture of 5.79 g (15.0 mmol) of bis(2,6-dimethyl-4-tert-butylphenyl)disulfide and 8.7 g (58.1 mmol) of spray-dried potassium fluoride (KF) in 30 ml of dry acetonitrile cooled on an ice bath. After 1.18 L (52.5 mmol) of chlorine was passed, nitrogen was passed through at the rate of 25 ml/min for two hours. The reaction mixture was filtered in a dry atmosphere. The filtrate was evaporated under vacuum (10-20 mmHg) at 20° C. and the residue distilled at reduced pressure to give 2,6-dimethyl-4-tert-butylphenylsulfur trifluoride (see Formula IV, Table 3) (bp 68-70° C./0.1 mmHg (4.1 g, 55% yield, purity of >97.4%)). Spectral data was the same as shown in Example 2.

The present example illustrates the utility of the present invention for synthesizing fluorinating agents that can be used to produce fluorine-containing compounds.

Example 4

Synthesis Embodiment of 4-tert-butylphenylsulfur trifluoride, A Fluorinating Agent of the Present Invention The following reaction scheme is, provided as illustrative for this example:

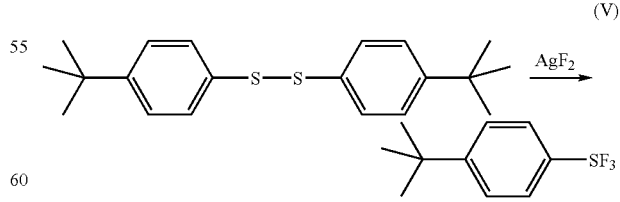

(V)

Using a synthesis procedure similar to the one described in Example 2,4-tert-butylphenylsulfur trifluoride was prepared. However, unlike in Example 2, bis(4-tert-butylphenyl)disulfide was added to the slurry instead of the bis(2,6-dimethyl-4-tert-butylphenyl)disulfide.

The above described synthesis procedure produced 4-tert-butylphenylsulfur trifluoride (see Formula V, Table 3). The physical and spectral data of the material are as follows: Bp 76° C./1 mmHg; $^{19}$F NMR (CD$_3$CN) δ 56.57 (br.s, 2F), −39.24 (br.s, 1F); $^1$H NMR (CD$_3$CN) δ 7.95 (d, J=8.3 Hz, 2H), 7.67 (d, J=8.3 Hz, 2H), 1.33 (s, 9H); $^{13}$C NMR (CD$_3$CN) δ 158.17 (s), 143.11 (s), 126.46 (s), 124.24 (s), 35.07 (s), 30.31 (s); MS (EI) m/z 222.1 (M$^+$, 0.4), 203.1 (M$^+$-F, 8.8), 137.1 (M$^+$-SF$_2$—CH$_3$, 100.0); HRMS (EI) for C$_{10}$H$_{13}$F$_3$S (M$^+$): found 222.068288, calcd 222.069007.

The present example illustrates the utility of the present invention for synthesizing fluorinating agents that can be used to produce fluorine-containing compounds.

Example 5

Synthesis Embodiment of 4-tert-butylphenylsulfur trifluoride, A Fluorinating Agent of the Present Invention The following reaction scheme is provided as illustrative for this example:

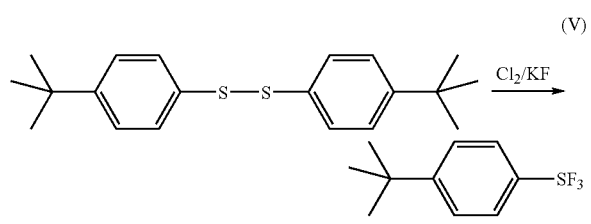

(V)

Using a synthesis procedure similar to the one described in Example 3,4-tert-butylphenylsulfur trifluoride was prepared. However, unlike in Example 3, bis(4-tert-butylphenyl)disulfide was used as a starting material. A yield of 67% was obtained.

The physical and spectral data for the product produced in this Example was the same as shown in Example 4.

The present example illustrates the utility of the present invention for synthesizing fluorinating agents that can be used to produce fluorine-containing compounds.

Example 6

Synthesis Embodiment of 2,4,6-trimethylphenylsulfur trifluoride, A Fluorinating Agent of the Present Invention The following reaction scheme is provided as illustrative for this example:

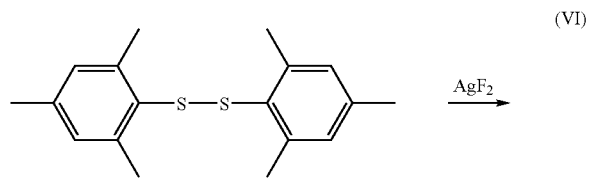

(VI)

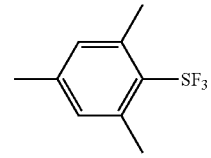

Using a synthesis procedure similar to the one described in Example 2,2,4,6-trimethylphenylsulfur trifluoride was prepared. However, unlike in Example 2, bis(2,4,6-trimethylphenyl)disulfide was added to the slurry instead of the bis(2,6-dimethyl-4-tert-butylphenyl)disulfide.

The above described synthesis procedure produced 2,4,6-trimethylphenylsulfur trifluoride (see Formula VIII, Table 3). The physical and spectral data of the material are as follows: Bp 58-59° C./1 mmHg; $^{19}$F NMR (THF-d$_8$) δ 53.13 (d, J=52.0 Hz, 2F), −57.40 (t, J=43.4 Hz, 1F); $^1$H NMR (CD$_3$CN/THF-d$_8$) δ 6.97 (s, 1H), 6.94 (s, 1H), 2.59 (s, 3H), 2.47(s, 3H), 2.24 (s); $^{13}$C NMR (THF-d$_8$) δ 142.33 (s), 141.83 (s), 134.20 (s), 133.03 (s), 130.86 (s), 129.99 (s), 20.07 (s), 18.83 (s), 18.70 (s); MS (EI) m/z 208.0 (M$^+$, 5.0), 189.0 (M$^+$-F, 15.4), 138.0 (M$^+$-SF$_2$, 100.0); HRMS (EI) for C$_9$H$_{11}$F$_3$S (M$^+$): found 208.052377, calcd 208.053357.

The present example illustrates the utility of the present invention for synthesizing fluorinating agents that can be used to produce fluorine-containing compounds.

Example 7

Synthesis Embodiment of 2,4,6-trimethylphenylsulfur trifluoride, A Fluorinating Agent of the Present Invention The following reaction scheme is provided as illustrative for this example:

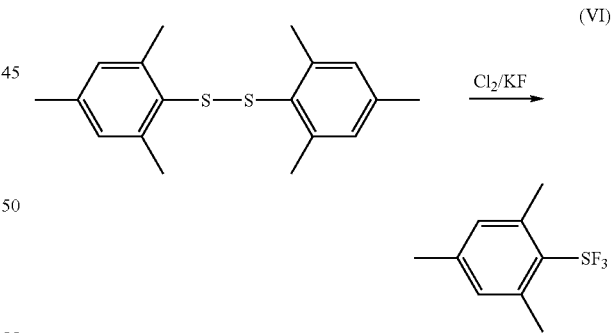

(VI)

Using a synthesis procedure similar to the one described in Example 3,2,4,6-trimethylphenylsulfur trifluoride was prepared. However, unlike in Example 2, bis(2,4,6-trimethylphenyl)disulfide was used as a starting material. A yield of 58% was obtained.

The physical and spectral data for the product produced in this Example was the same as shown in Example 6.

The present example illustrates the utility of the present invention for synthesizing fluorinating agents that can be used to produce fluorine-containing compounds.

Example 8

Synthesis Embodiment of 2,4-dimethylphenylsulfur trifluoride, A Fluorinating Agent of the Present Invention The following reaction scheme is provided as illustrative for this example:

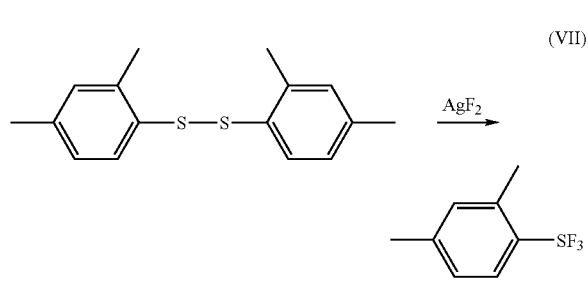

(VII)

AgF$_2$

Using a synthesis procedure similar to the one described in Example 2, 2,4-dimethylphenylsulfur trifluoride was prepared. However, unlike in Example 2, bis(2,4-dimethylphenyl)disulfide was added to the slurry instead of the bis(2,6-dimethyl-4-tert-butylphenyl)disulfide. A yield of 59% was obtained.

The above described synthesis procedure produced 2,4-dimethylphenylsulfur trifluoride (see Formula VIII, Table 3). The physical and spectral data of the material are as follows: Bp 56° C./1 mmHg; $^{19}$F NMR (CD$_3$CN/THF-d$_8$) δ 52.44 (d, J=60.7 Hz, 2F), −57.75 (t, J=60.7 Hz, 1F); $^1$H NMR (CD$_3$CN) δ 7.90 (d, J=8.2 Hz, 1H), 7.29 (d, J=8.2 Hz, 1H), 7.18 (s, 1H), 2.62 (s, 3H), 2.42 (s, 3H); $^{13}$C NMR (CD$_3$CN/THF-d$_8$) δ 144.76 (s), 134.30 (s), 133.80 (s), 131.92 (s), 131.70 (s), 129.79 (s), 19.09 (s), 18.92 (s); MS (EI) m/z 194.0 (M$^+$, 6.9), 175.0 (M$^+$-F, 22.4), 124.0 (M$^+$-SF$_2$, 100.0); HRMS (EI) for C$_8$H$_9$F$_3$S (M$^+$): found 194.036951, calcd 194.037707.

The present example illustrates the utility of the present invention for synthesizing fluorinating agents that can be used to produce fluorine-containing compounds.

Example 9

Synthesis Embodiment of 2,4-dimethylphenylsulfur trifluoride, A Fluorinating Agent of the Present Invention The following reaction scheme is provided as illustrative for this example:

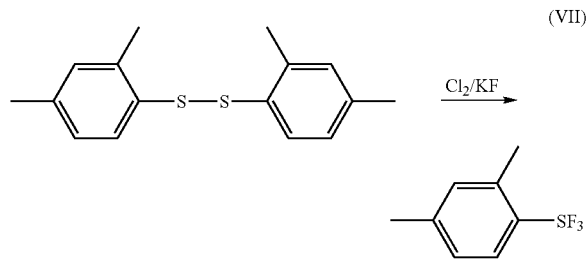

(VII)

Cl$_2$/KF

Using a synthesis procedure similar to the one described in Example 3, 2,4-dimethylphenylsulfur trifluoride was prepared. However, unlike in Example 3, bis(2,4-dimethylphenyl)disulfide was used as a starting material. A yield of 71% was obtained.

The physical and spectral data for the product in this Example were the same as shown in Example 8.

The present example illustrates the utility of the present invention for synthesizing fluorinating agents that can be used to produce fluorine-containing compounds.

Example 10

Synthesis Embodiment of 2,5-dimethylphenylsulfur trifluoride, A Fluorinating Agent of the Present Invention The following reaction scheme is provided as illustrative for this example:

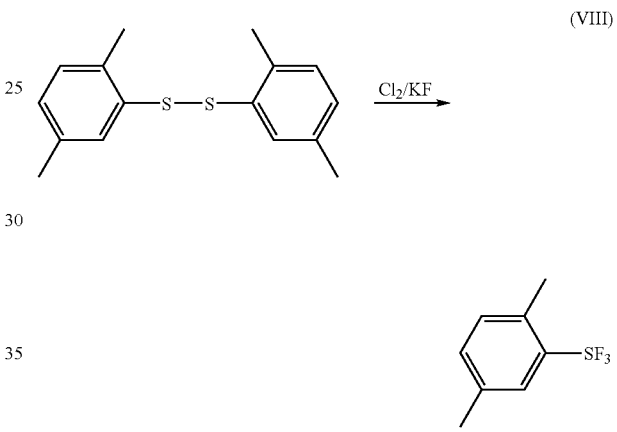

(VIII)

Cl$_2$/KF

Using a synthesis procedure similar to the one described in Example 3, 2,5-dimethylphenylsulfur trifluoride was prepared. However, unlike in Example 3, bis(2,5-dimethylphenyl)disulfide was used as a starting material. A yield of 60% was obtained. The above described synthesis procedure produced 2,5-dimethylphenylsulfur trifluoride (see Formula VIII, Table 3). The physical and spectral data of the material are as follows: Bp 76-79° C./3 mmHg; $^{19}$F NMR (CD$_3$CN) δ 60.89 (br. s, 2F), −57.15 (br. s, 1F); $^1$H NMR (CD$_3$CN) δ 7.90 (s, 1H), 7.36 (d, J=7.7 Hz, 1H), 7.26 (d, J=7.7 Hz, 1H), 2.66 (s, 3H), 2.49 (s, 3H); MS (EI) m/z 105.1 (M$^+$-SF$_3$, 100.0), 194.0 (M$^+$, 8.0); HRMS (EI) for C$_8$H$_9$F$_3$S (M$^+$): found 194.037412, calcd 194.037707.

The present example illustrates the utility of the present invention for synthesizing fluorinating agents that can be used to produce fluorine-containing compounds.

Example 11

Synthesis Embodiment of 2,6-dimethylphenylsulfur trifluoride, A Fluorinating Agent of the Present Invention The following reaction scheme is provided as illustrative for this example:

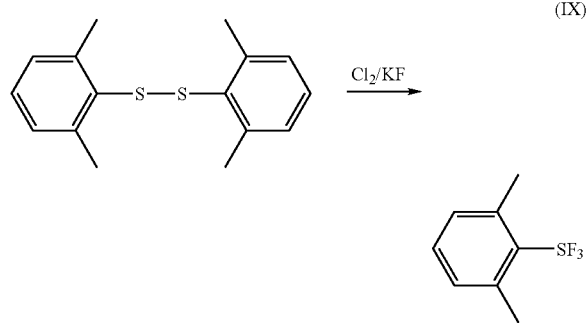

(IX)

Using a synthesis procedure similar to the one described in Example 3, 2,6-dimethylphenylsulfur trifluoride was prepared. However, unlike in Example 3, bis(2,6-dimethylphenyl)disulfide was used as a starting material. A yield of 75% was obtained. The above described synthesis procedure produced 2,6-dimethylphenylsulfur trifluoride (see Formula IX, Table 3). The physical and spectral data of the material are as follows: Bp 73-75° C./3.5 mmHg; $^{19}$F NMR (CD$_3$CN) δ 53.51 (br.s, 2F), −55.99 (br.s, 1F); $^1$H NMR (CD$_3$CN) δ 7.41 (t, J=7.7 Hz, 1H), 7.23 (br.s, 2H), 2.86 (s, 3H), 2.70 (s, 3H); MS (EI) m/z 105.1 (M$^+$-SF$_3$, 100.0), 194.0 (M$^+$, 7.0); HRMS (EI) for C$_8$H$_9$F$_3$S (M$^+$): found 194.037035, calcd 194.037707.

The present example illustrates the utility of the present invention for synthesizing fluorinating agents that can be used to produce fluorine-containing compounds.

Example 12

Synthesis Embodiment of 4-fluorophenylsulfur trifluoride, A Fluorinating Agent of the Present Invention The following reaction scheme is provided as illustrative for this example:

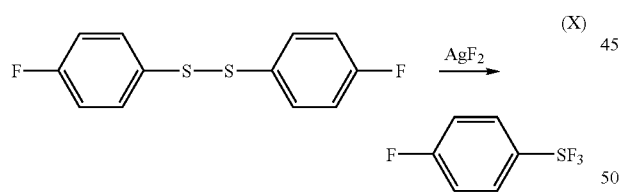

(X)

Using a synthesis procedure similar to the one described in Example 2, 4-fluorophenylsulfur trifluoride was prepared. However, unlike in Example 2, bis(4-fluorophenyl) disulfide was used as a starting material. A yield of 56% was obtained.

The above described synthesis procedure produced 4-fluorophenylsulfur trifluoride (see Formula X, Table 3). The physical and spectral data of the material are as follows: Bp 39-40° C./2 mmHg; $^{19}$F NMR (CD$_3$CN/THF-d$_8$) δ 58.14 (d, J=60.7 Hz, 2F), −37.28 (t, J=32.0 Hz, 1F), −104.42 (s, 1F); $^1$H NMR (CD$_3$CN/THF-d$_8$) δ 8.40 (dd, J=5.8, 8.6 Hz, 2H), 7.66 (t, J=8.6 Hz, 2H); $^{13}$C NMR (CD$_3$CN/THF-d$_8$) δ 165.98 (d, J=255.0 Hz), 142.41 (d, J=15.2 Hz), 130.66 (d, J=8.0 Hz), 116.69 (d, J=23.1 Hz); MS (EI) m/z 184.0 (M$^+$-F, 0.1), 165.0 (M$^+$-F, 18.5), 114.0 (M$^+$-SF$_2$, 100.0); HRMS (EI) for C$_6$H$_4$F$_4$S (M$^+$): found 183.996675, calcd 183.996985.

The present example illustrates the utility of the present invention for synthesizing fluorinating agents that can be used to produce fluorine-containing compounds.

Example 13

Synthesis Embodiment of 4-chlorophenylsulfur trifluoride, A Fluorinating Agent of the Present Invention The following reaction scheme is provided as illustrative for this example:

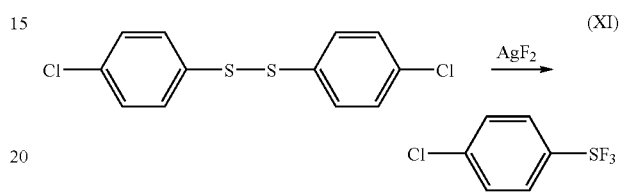

(XI)

Using a synthesis procedure similar to the one described in Example 2, 4-chlorophenylsulfur triflouride was prepared. However, unlike Example 2, bis(4-chlorophenyl) disulfide was used as a starting material. A yield of 32% was obtained.

The above described synthesis procedure produced 4-chlorophenylsulfur trifluoride (see Formula XI, Table 3). The physical and spectral data of the material are as follows: Bp 55-56° C./1 mmHg; $^{19}$F NMR (CD$_3$CN/THF-d$_8$) δ 58.20 (d, J=60.7 Hz, 2F), −39.44 (t, J=60.7 Hz, 1F); $^1$H NMR (CD$_3$CN/THF-d$_8$) δ 8.19 (d, J=7.6 Hz, 2H), 7.82 (d, J=7.6 Hz, 2H); $^{13}$C NMR (CD$_3$CN) δ 144.65 (s), 140.00 (s), 129.56 (s), 128.38 (s); MS (EI) m/z 201.9 (M$^+$, 0.3), 199.9 (M$^+$, 0.9), 130.0 (M$^+$-SF$_2$, 100.0), HRMS (EI) for C$_6$H$_4$ClF$_3$S (M$^+$): found 201.965496, calcd. 201.964484, and found 199.967032, calcd 199.967434.

The present example illustrates the utility of the present invention for synthesizing fluorinating agents that can be used to produce fluorine-containing compounds.

Example 14

Synthesis Embodiment of 3-methyl-4-chlorophenylsulfur trifluoride, A Fluorinating Agent of the Present Invention The following reaction scheme is provided as illustrative for this example:

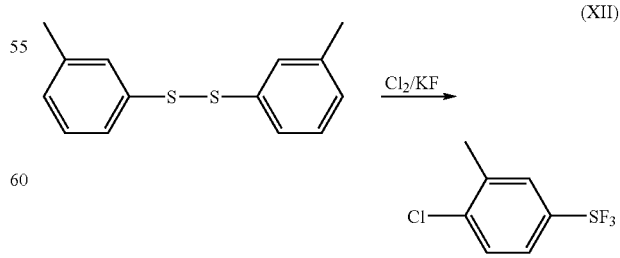

(XII)

Chlorine (Cl$_2$) was passed at a rate of 30 ml/min into a stirred mixture of 4.44 g (18 mmol) of bis(3-methylphenyl) disulfide and 15.7 g (270 mmol) of spray-dried KF. The stirred mixture also included 100 ml of dry acetonitrile. The mixture was stirred on an ice bath. After 1.92 L (85.7 mmol) of chlorine was passed through the mixture, nitrogen was then passed through the mixture for 3 hours at room temperature. The reaction mixture was then filtered in a dry atmosphere and the filtrate was evaporated under reduced pressure without heating.

Residue was distilled at reduced pressure to give 4.71 g of the compound as shown in Formula XII, Table 3. A yield of 61% was obtained. The physical and spectral data of the material are as follows: Bp 72-75° C./4 mmHg, $^{19}$F NMR (CDCl$_3$) δ 57.9 (br.s, 2F), −37.7 (br.s, 1F); $^1$H NMR (CDCl$_3$) δ 7.85 (br.s, 1H), 7.73 (d, J=8.6 Hz, 1H), 7.46 (d, J=8.6 Hz, 1H), 2.30 (s, 3H); MS (EI) m/z 125.0 (M$^+$-SF$_3$, 100.0), 214 (M$^+$, 1.2); HRMA (EI) for C$_7$H$_6$ClF$_3$S (M$^+$): found 215.980817, calcd 215.980134, and found 213.983426, calcd 213.983085.

The present example illustrates the utility of the present invention for synthesizing fluorinating agents that can be used to produce fluorine-containing compounds.

Example 15

Synthesis Embodiment of 2,46-tri(isopropyl)phenylsulfur trifluoride, A Fluorinating Agent of the Present Invention The following reaction scheme is provided as illustrative for this example:

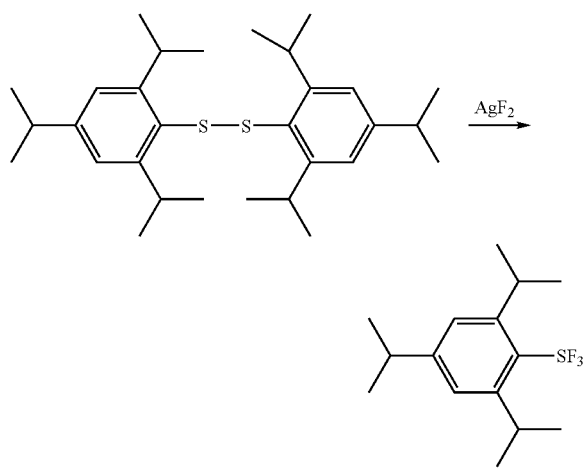

(XIII)

In a similar way as in Example 2,2,4,6-tri(isopropyl) phenylsulfur trifluoride was synthesized from bis[2,4,6-tris (isopropyl)phenyl]disulfide in 79% yield. The purification of this compound was achieved by sublimation at 70° C./0.1 mmHg. The formula is shown as Formula XIII, Table 3.

The physical and spectral data of the material are shown in the following: Mp 87.3° C. (by DSC); $^{19}$F NMR (THF-d$_8$) δ 60.68 (d, J=52.0 Hz, 2F), −53.88 (t, J=52.0 Hz, 1F); $^1$H NMR (CD$_3$CN) δ 7.33 (s, 1H), 7.27 (s, 1H), 3.89 (m, 1H), 3.44 (m, 1H), 2.95 (septet, J=7.1 Hz, 1H), 1.29 (d, J=6.6 Hz, 12H), 1.24 (d, J=7.1 Hz, 6H); MS (EI) m/z 149.0 (M$^+$+1-2F, 100.0), 292.2 (M$^+$, 1.2); HRMS (EI) for C$_{15}$H$_{23}$F$_3$S (M$^+$): found 292.145944, calcd 292.147257.

The present example illustrates the utility of the present invention for synthesizing fluorinating agents that can be used to produce fluorine-containing compounds.

Examples 16-25

Thermal Analysis of Substituted Phenylsulfur Trifluorides

Thermal analysis was performed on compounds IV-XIII (Table 3) of the present invention. Decomposition temperature and exothermic heat (−ΔH) of each compound was determined using Differential Scanning Spectroscopy, i.e., using a Differential Scanning Spectrometer (DSC).

The decomposition temperature is the temperature at which onset of decomposition begins, and the exothermic heat is the amount of heat that results from the compounds decomposition. In general, a higher decomposition temperature and lower exothermic heat value provide compounds having greater thermal stability and provide greater safety.

Table 4 illustrates that the compounds of the present invention show unexpected and significant improvement in decomposition temperature and exothermic heat values over conventional fluorinating agents (DAST and Deoxo-Fluor®). This data illustrates the improved thermal stability of the compounds of the invention and, as a result, the improved safety of the compounds of the invention over other conventional fluorinating agents.

TABLE 4

Thermal analysis data of substituted phenylsulfur trifluorides (Formulas IV–XIII) and prior art DAST and Deoxo-Fluor®

| | Compound | Decomposition temp. (° C.) | −ΔH(J/g) |
|---|---|---|---|
| Ex. 16 | IV; $R^{1a} = R^{1b} = CH_3$, $R^{2a} = R^{2b} =$ H, $R^3 = C(CH_3)_3$ | 232 | 544 |
| Ex. 17 | V; $R^{1a} = R^{1b} = R^{2a} = R^{2b} =$ H, $R^3 = C(CH_3)_3$ | 319 | 700 |
| Ex. 18 | VI; $R^{1a} = R^{1b} = CH_3$, $R^{2a} = R^{2b} =$ H, $R^3 = CH_3$ | 209 | 462 |
| Ex. 19 | VII; $R^{1a} = CH_3$ $R^{1b} =$ H, $R^{2a} = R^{2b} =$ H, $R^3 = CH_3$ | 222 | 625 |
| Ex. 20 | VIII; $R^{1a} = CH_3$, $R^{1b} =$ H, $R^{2a} =$ H, $R^{2b} = CH_3$, $R^3 =$ H | 228 | 486 |
| Ex. 21 | IX; $R^{1a} = R^{1b} = CH_3$, $R^{2a} = R^{2b} =$ $R^3 =$ H | 225 | 595 |
| Ex. 22 | X; $R^{1a} = R^{1b} = R^{2a} = R^{2b} =$ H, $R^3 =$ F | 297 | 368 |
| Ex. 23 | XI; $R^{1a} = R^{1b} = R^{2a} = R^{2b} =$ H, $R^3 =$ Cl | 311 | 458 |
| Ex. 24 | XII; $R^{1a} = R^{1b} =$ H, $R^{2a} = CH_3$, $R^{2b} =$ H, $R^3 =$ Cl | 299 | 391 |
| Ex. 25 | XIII; $R^{1a} = R^{1b} = CH(CH_3)_2$, $R^{2a} = R^{2b} =$ H, $R^3 = CH(CH_3)_2$ | 215 | 552 |
| | $(C_2H_5)_2N$—SF$_3$ (DAST) | ~140 | 1700 |
| | $(CH_3OCH_2CH_2)_2N$—SF$_3$ (Deoxo-Fluor®) | ~140 | 1100 |

Examples 26-55

Fluorination of Target Compounds Using the Compounds of the Present Invention

Several procedures are provided for fluorinating a target compound using the fluorinating agents of the present invention. Four procedures are described as procedures A-D:

Procedure A: In a 10 ml fluoropolymer-bottle (equipped with an N$_2$ inlet tube, septum and magnetic stir bar): 65 mg of benzyl alcohol (0.604 mmol) was added to a solution of 166 mg 2,6-dimethyl-4-tert-butylphenylsulfur trifluoride (formula IV) (0.664 mmol) in 3 ml anhydrous CH$_2$Cl$_2$. The addition was performed at room temperature under a stream of $N_2$. The mixture was allowed to stir at room temperature. The progress of the reaction was monitored by gas chromatography (GC). After 2 hours a $^{19}$F-NMR analysis was performed indicating that benzyl fluoride was obtained (88% yield).

Procedure B: In a 5 ml fluoropolymer-bottle (equipped with an $N_2$ inlet tube, septum and magnetic stir bar): 42 mg isovaleraldehyde (0.491 mmol) was added to a solution of 135 mg 2,6-dimethyl-4-tert-butylphenylsulfur trifluoride (formula IV) (0.540 mmol) in 0.5 ml anhydrous $CH_2Cl_2$. The addition was performed at room temperature under a stream of $N_2$. The mixture was allowed to stir at room temperature. The progress of the reaction was monitored by GC. After 24 hours a $^{19}$F-NMR analysis was performed indicating that 1,1-difluoro-3-methylbutane was obtained (95% yield).

Procedure C: In a 5 ml fluoropolymer-bottle (equipped with an $N_2$ inlet tube, septum and magnetic stir bar): 40 mg cyclohexanone (0.405 mmol) was added to a solution of 172 mg 2,6-dimethyl-4-tert-butylphenylsulfur trifluoride (formula IV) (0.688 mmol) in 0.5 ml anhydrous $CH_2Cl_2$. The addition was performed at room temperature under a stream of $N_2$. Ethanol (3.7 mg, 0.08 mmol) was added to the reaction and the reaction allowed to stir at room temperature. The progress of the reaction was monitored by GC. After 24 hours a $^{19}$F-NMR analysis was performed indicating that 1,1-difluorocyclohexane was obtained (74% yield).

Procedure D: In a 1 ml sealed fluoropolymer tube: 21 mg benzoic acid (0.170 mmol) was added to 106 mg 2,6-dimethyl-4-tert-butylphenylsulfur trifluoride (formula IV) (0.424 mmol). The combination was made at room temperature under a stream of $N_2$. The tube was then stirred at 100° C. The progress of the reaction was monitored by GC. After 2 hours a $^{19}$F-NMR analysis was performed indicating that α,α,α-trifluorotoluene was obtained (88% yield).

Referring to Table 5: Examples 26-44, 54, 55 and reactions with a conventional fluorinating agent ($PhSF_3$) and a known and similar compound (p-$CH_3C_6H_5SF_3$) (J. Am. Chem. Soc., Vol. 84, pp 3058-3063 (1962)) were carried out under the reaction conditions shown in Table 5 according to procedure A; examples 45 and 48-50 were carried out under the reaction conditions shown in Table 5 according to procedure B; examples 46 and 47 were carried out under the conditions shown in Table 5 according to procedure C; and examples 51-53 were carried out under the conditions shown in Table 5 according to procedure D.

TABLE 5

Fluorinations of various organic target compounds with substituted phenylsulfur trifluorides (Formulas IV~XIII) and prior art compounds ($PhSF_3$ and p-$CH_3C_6H_5SF_3$)

| | Phenylsulfur trifluorides | Organic compounds | Reaction Conditions | | Fluorinated Compounds | Yield |
|---|---|---|---|---|---|---|
| | | | Solv. Temp. | Time | Chemical structure | |
| | $PhSF_3$ | $PhCH_2OH$ | $CH_2Cl_2$ r.t. | 2 h | $PhCH_2F$ | 25% |
| | p-$CH_3C_6H_5SF_3$ | $PhCH_2OH$ | $CH_2Cl_2$ r.t. | 2 h | $PhCH_2F$ | 19% |
| Ex. 26 | IV | $PhCH_2OH$ | $CH_2Cl_2$ r.t. | 2 h | $PhCH_2F$ | 88% |
| Ex. 27 | V | $PhCH_2OH$ | $CH_2CL_2$ r.t. | 2 h | $PhCH_2F$ | 52% |
| Ex. 28 | VI | $PhCH_2OH$ | $CH_2Cl_2$ r.t. | 2 h | $PhCH_2F$ | 38% |
| Ex. 29 | VII | $PhCH_2OH$ | $CH_2Cl_2$ r.t. | 2 h | $PhCH_2F$ | 46% |
| Ex. 30 | IX | $PhCH_2OH$ | $CH_2Cl_2$ r.t. | 2 h | $PhCH_2F$ | 40% |
| Ex. 31 | XI | $PhCH_2OH$ | $CH_2Cl_2$ r.t. | 2 h | $PhCH_2F$ | 37% |
| Ex. 32 | XIII | $PhCH_2OH$ | $CH_2Cl_2$ r.t. | 2 h | $PhCH_2F$ | 46% |
| Ex. 33 | IV | n-$C_{12}H_{25}OH$ | $CH_2Cl_2$ r.t. | 6 h | n-$C_{12}H_{25}F$ | 91% |
| Ex. 34 | V | n-$C_{12}H_{25}OH$ | $CH_2Cl_2$ r.t. | 6 h | n-$C_{12}H_{25}F$ | 77% |
| Ex. 35 | VI | n-$C_{12}H_{25}OH$ | $CH_2Cl_2$ r.t. | 6 h | n-$C_{12}H_{25}F$ | 61% |
| Ex. 36 | VII | n-$C_{12}H_{25}OH$ | $CH_2Cl_2$ r.t. | 6 h | n-$C_{12}H_{25}F$ | 68% |
| Ex. 37 | X | n-$C_{12}H_{25}OH$ | $CH_2Cl_2$ r.t. | 6 h | n-$C_{12}H_{25}F$ | 66% |
| Ex. 38 | XI | n-$C_{12}H_{25}OH$ | $CH_2Cl_2$ r.t. | 6 h | n-$C_{12}H_{25}F$ | 66% |
| Ex. 39 | IV | n-$C_{10}H_{21}CH(OH)CH_3$ | $CH_2Cl_2$ r.t. | 6 h | n-$C_{10}H_{21}CHFCH_3$ | 75% |
| Ex. 40 | V | n-$C_{10}H_{21}CH(OH)CH_3$ | $CH_2Cl_2$ r.t. | 6 h | n-$C_{10}H_{21}CHFCH_3$ | 72% |
| Ex. 41 | VI | n-$C_{10}H_{21}CH(OH)CH_3$ | $CH_2Cl_2$ r.t. | 6 h | n-$C_{10}H_{21}CHFCH_3$ | 70% |
| Ex. 42 | VII | n-$C_{10}H_{21}CH(OH)CH_3$ | $CH_2Cl_2$ r.t. | 6 h | n-$C_{10}H_{21}CHFCH_3$ | 54% |
| Ex. 43 | X | n-$C_{10}H_{21}CH(OH)CH_3$ | $CH_2Cl_2$ r.t. | 6 h | n-$C_{10}H_{21}CHFCH_3$ | 49% |
| Ex. 44 | XI | n-$C_{10}H_{21}CH(OH)CH_3$ | $CH_2Cl_2$ r.t. | 6 h | n-$C_{10}H_{21}CHFCH_3$ | 47% |
| Ex. 45 | IV | $(CH_3)_2CHCH_2CHO$ | $CH_2Cl_2$ r.t. | 1 day | $(CH_3)_2CHCH_2CF_2H$ | 95% |
| Ex. 46 | IV | Cyclohexanone | $CH_2Cl_2$ r.t. | 1 day | 1,1-diF-cyclohexane | 74% |
| Ex. 47 | IV | n-$C_{11}H_{23}COCH_3$ | $CH_2Cl_2$ r.t. | 1 day | n-$C_{11}H_{23}CF_2CH_3$ | 100% |
| Ex. 48 | IV | PhCOOH | $CH_2Cl_2$ r.t. | 2 day | PhCOF | 100% |
| Ex. 49 | IV | n-$C_{11}H_{23}COOH$ | $CH_2Cl_2$ r.t. | 1 day | n-$C_{11}H_{23}COF$ | 97% |
| Ex. 50 | IV | PhCOCl | $CH_2Cl_2$ r.t. | 2 day | PhCOF | 51% |
| Ex. 51 | IV | PhCOOH | Non 100° C. | 2 h | $PhCF_3$ | 89% |
| Ex. 52 | IV | p-(n-$C_7H_{15})C_6H_4COOH$ | Non 100° C. | 2 h | p-(n-$C_7H_{15})C_6H_4CF_3$ | 88% |
| Ex. 53 | IV | n-$C_{11}H_{23}COOH$ | Non 100° C. | 2 h | n-$C_{11}H_{23}CF_3$ | 55% |
| Ex. 54 | IV | $PhSCH_3$ | $CH_2Cl_2$ r.t. | 20 min | $PhSCH_2F$ | 61% |
| Ex. 55 | IV | $PhSOCH_3$ | $CH_2Cl_2$ r.t. | 24 h | $PhSCH_2F$ | 41% |

$PhSF_3$ = phenylsulfur trifluoride; p-$CH_3C_6H_4SF_3$ = p-methylphenylsulfur trifluoride; r.t. = room temperature; Non = No solvent; p-(n-$C_7H_{15})C_6H_4COOH$ = p-(n-heptyl)benzoic acid; $PhSCH_3$ = thioanisole; $PhSOCH_3$ = methyl phenyl sulfoxide.

As shown from the data in Table 5, it has been unexpectedly shown that the novel substituted phenylsulfur trifluorides of the invention are much more effective fluorinating agents than conventional fluorinating agents. In addition, the present examples illustrate that the novel compounds of the invention can fluorinate a wide variety of target compounds with high yields.

It is understood for purposes of this disclosure, that various changes and modifications may be made to the invention that are well within the scope of the invention. Numerous other changes may be made which will readily suggest themselves to those skilled in the art which are encompassed in the spirit of the invention disclosed herein and as defined in the appended claims.

This specification contains numerous citations to references such as patents, patent applications, and publications. Each is hereby incorporated by reference for all purposes.

What is claimed is:

1. A compound of the formula (I):

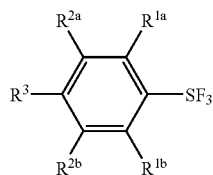

in which
$R^{1a}$ and $R^{1b}$ are independently a hydrogen atom or a primary or secondary alkyl group having from one to eight carbon atoms;
$R^{2a}$ and $R^{2b}$ are independently a hydrogen atom or a primary, secondary, or tertiary alkyl group having from one to eight carbon atoms; and
$R^3$ is a hydrogen atom, a halogen atom, or a primary, secondary, or tertiary alkyl group having from one to eight carbon atoms;
wherein, when $R^3$ is a hydrogen atom, at least two of $R^{1a}$, $R^{1b}$, $R^{2a}$, and $R^{2b}$ are primary, secondary, or tertiary alkyl groups having from one to eight carbon atoms and the others are a hydrogen atom, and wherein, when $R^3$ is a primary alkyl group having from one to eight carbon atoms, at least one of $R^{1a}$, $R^{1b}$, $R^{2a}$, and $R^{2b}$ is a primary, secondary, or tertiary alkyl group having from one to eight carbon atoms and the others are a hydrogen atom, and wherein when at least two of $R^{2a}$, $R^{2b}$, and $R^3$ are tertiary alkyl groups, the tertiary alkyl groups are non-adjacent.

2. The compound of claim 1, wherein the primary, secondary, or tertiary alkyl groups have from one to four carbon atoms.

3. The compound of claim 1, wherein $R^3$ is a tertiary alkyl group.

4. The compound of claim 3, wherein the tertiary group is tert-butyl group.

5. The compound of claim 1, wherein the compound is selected from the group consisting of 2,6-dimethyl-4-tert-butylphenylsulfur trifluoride; 4-tert-butylphenylsulfur trifluoride; 2,4,6-trimethylphenylsulfur trifluoride; 2,4-dimethylphenylsulfur trifluoride; 2,5-dimethylphenylsulfur trifluoride; 2,6-dimethylphenylsulfur trifluoride; 4-fluorophenylsulfur trifluoride; 4-chlorophenylsulfur trifluoride; 3-methyl-4-chlorophenylsulfur trifluoride; and 2,4,6-tri(isopropyl)phenylsulfur trifluoride.

6. The compound of claim 1, wherein the compound is 2,6-dimethyl-4-tert-butylphenylsulfur trifluoride.

7. A compound according to claim 1, wherein the compound is a compound of the formula (II):

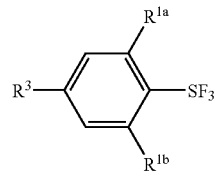

in which:
$R^{1a}$ and $R^{1b}$ are independently a hydrogen atom or a primary or secondary alkyl group having from one to eight carbon atoms; and
$R^3$ is a hydrogen atom, a halogen atom, or a primary, secondary, or tertiary alkyl group having from one to eight carbon atoms;
wherein when $R^3$ is a hydrogen atom, $R^{1a}$ and $R^{1b}$ are independently a primary or secondary alkyl group having from one to eight carbon atoms, and wherein, when $R^3$ is a primary alkyl group having one to eight carbon atoms, at least one of $R^{1a}$ and $R^{1b}$ is a primary or secondary alkyl group having from one to eight carbon atoms and the other is a hydrogen atom.

8. The compound of claim 7, wherein the primary, secondary, or tertiary alkyl groups have from one to four carbon atoms.

9. The compound of claim 7, wherein $R^3$ is a tertiary alkyl group.

10. The compound of claim 9, wherein the tertiary group is tert-butyl group.

11. A method of introducing one or more fluorine atoms into a target compound comprising:
contacting a fluorinating agent of formula (I) from claim 1 with the target compound under conditions that allow one or more fluorine atoms to be introduced into the target compound.

12. The method of claim 11, wherein the target compound has one or more oxygen or oxygen-containing groups which are replaced by the introduction of the one or more fluorine atoms.

13. The method of claim 11, wherein the fluorinating agent is selected from the group consisting of 2,6-dimethyl-4-tert-butylphenylsulfur trifluoride; 4-tert-butylphenylsulfur trifluoride; 2,4,6-trimethylphenylsulfur trifluoride; 2,4-dimethylphenylsulfur trifluoride; 2,5-dimethylphenylsulfur trifluoride; 2,6-dimethylphenylsulfur trifluoride; 4-fluorophenylsulfur trifluoride; 4-chlorophenylsulfur trifluoride; 3-methyl-4-chlorophenylsulfur trifluoride; and 2,4,6-tri(isopropyl)phenylsulfur trifluoride.

14. The method of claim 11, wherein the fluorinating agent is 2,6-dimethyl-4-tert-butylphenylsulfur trifluoride.

15. A method of introducing one or more fluorine atoms into a target compound comprising:
contacting a fluorinating agent of formula (II) from claim 7 with the target compound under conditions that allow one or more fluorine atoms to be introduced into the target compound.

16. The method of claim 15, wherein the target compound has one or more oxygen or oxygen-containing groups which are replaced by the introduction of the one or more fluorine atoms.

* * * * *

UNITED STATES PATENT AND TRADEMARK OFFICE
CERTIFICATE OF CORRECTION

PATENT NO.        : 7,265,247 B1
APPLICATION NO.   : 11/494983
DATED             : September 4, 2007
INVENTOR(S)       : Teruo Umemoto It is certified that error appears in the above-identified patent and that said Letters Patent is hereby corrected as shown below:

Column 4, line 30 should be corrected to read "Examples of preferred halogen atoms of $R^3$ include: fluo-".

Column 5, line 57 should be corrected to read "carbon atoms, provided that, when $R^3$ is a hydrogen atom, $R^{1a}$ and".

Column 8, line 12 should be corrected to read "values of 1100-1700 J/g as compared to compounds of the".

Column 9, under Example 1, the compound number (III) should be moved from the upper right of the reaction scheme to a position below the final product in the reaction scheme.

Column 11, under Example 2, the compound number (IV) should be moved from the upper right of the reaction scheme to a position below the final product in the reaction scheme.

Column 12, under Example 3, the compound number (IV) should be moved from the upper right of the reaction scheme to a position below the final product in the reaction scheme; line 50 should be corrected to read "The following reaction scheme is provided as illustrative"; under Example 4, the compound number (V) should be moved from the upper right of the reaction scheme to a position below the final product in the reaction scheme; line 64 should be corrected to read "in Example 2, 4-tert-butylphenylsulfur trifluoride was pre-".

Column 13, line 10 should be corrected to read "($M^+$-F, 8.8), 137.1 ($M^+$-$SF_2$-$CH_3$, 100.0); HRMS (EI) for"; line 38 should be corrected to read "in Example 3, 4-tert-butylphenylsulfur trifluoride was pre-"; under Example 5, the compound number (V) should be moved from the upper right of the reaction scheme to a position below the final product in the reaction scheme; line 38 should be corrected to read "in Example 3, 4-tert-butylphenylsulfur trifluoride was pre-"; under Example 6, the compound number (VI) should be moved from the upper right of the reaction scheme to a position below the final product in the reaction scheme in column 14.

UNITED STATES PATENT AND TRADEMARK OFFICE
CERTIFICATE OF CORRECTION

PATENT NO.         : 7,265,247 B1
APPLICATION NO. : 11/494983
DATED                : September 4, 2007
INVENTOR(S)       : Teruo Umemoto It is certified that error appears in the above-identified patent and that said Letters Patent is hereby corrected as shown below:

Column 14, line 12 should be corrected to read "in Example 2, 2,4,6-trimethylphenylsulfur trifluoride was"; line 17 should be corrected to read "6-trimethylphenylsulfur trifluoride (see Formula VI, Table"; under Example 7, the compound number (VI) should be moved from the upper right of the reaction scheme to a position below the final product in the reaction scheme; line 58 should be corrected to read "in Example 3, 2,4,6-trimethylphenylsulfur trifluoride was"; line 59 should be corrected to read "prepared. However, unlike in Example 3, bis(2,4,6-trimeth-".

Column 15, under Example 8, the compound number (VII) should be moved from the upper right of the reaction scheme to a position below the final product in the reaction scheme; line 23 should be corrected to read "in Example 2, 2,4-dimethylphenylsulfur trifluoride was pre-"; line 29 should be corrected to read "dimethylphenylsulfur trifluoride (see Formula VII, Table"; under Example 9, the compound number (VII) should be moved from the upper right of the reaction scheme to a position below the final product in the reaction scheme; line 67 should be corrected to read "in Example 3, 2,4-dimethylphenylsulfur trifluoride was pre-".

Column 16, under Example 10, the compound number (VIII) should be moved from the upper right of the reaction scheme to a position below the final product in the reaction scheme; line 41 should be corrected to read "in Example 3, 2,5-dimethylphenylsulfur trifluoride was pre-".

Column 17, under Example 11, the compound number (IX) should be moved from the upper right of the reaction scheme to a position below the final product in the reaction scheme; line 18 should be corrected to read "in Example 3, 2,6-dimethylphenylsulfur trifluoride was pre-"; under Example 12, the compound number (X) should be moved from the upper right of the reaction scheme to a position below the final product in the reaction scheme.

UNITED STATES PATENT AND TRADEMARK OFFICE
CERTIFICATE OF CORRECTION

PATENT NO. : 7,265,247 B1
APPLICATION NO. : 11/494983
DATED : September 4, 2007
INVENTOR(S) : Teruo Umemoto It is certified that error appears in the above-identified patent and that said Letters Patent is hereby corrected as shown below:

Column 18, under Example 13, the compound number (XI) should be moved from the upper right of the reaction scheme to a position below the final product in the reaction scheme; under Example 14, the compound number (XII) should be moved from the upper right of the reaction scheme to a position below the final product in the reaction scheme.

Column 19, line 15 should be corrected to read "100.0), 214 ($M^+$, 1.2); HRMR (EI) for $C_7H_6ClF_3S$ ($M^+$):"; line 25 should be corrected to read "2,4,6-tri(isopropyl)phenylsulfur trifluoride, A"; under Example 15, the compound number (XIII) should be moved from the upper right of the reaction scheme to a position below the final product in the reaction scheme; line 52 should be corrected to read "In a similar way as in Example 2, 2,4,6-tri(isopropyl)".

Column 22, line 1 should be corrected to read "Procedure D: In a 1 ml fluoropolymer tube: 21 mg"; line 5 should be corrected to read "ture under a stream of $N_2$. The tube was sealed then stirred at 100°"; Table 5, at the row for *Ex. 27*, the entry under *Solv. Temp.* should be corrected to read "$CH_2Cl_2$ r.t."; Table 5, at the row for *Ex. 29*, the entry under *Phenylsulfur trifluorides* should be corrected to read "VIII".

Signed and Sealed this

Twenty-ninth Day of December, 2009

David J. Kappos
*Director of the United States Patent and Trademark Office*